US00PP29144P3

(12) United States Plant Patent
Stemkens

(10) Patent No.: US PP29,144 P3
(45) Date of Patent: Mar. 20, 2018

(54) ***CAMPANULA* PLANT NAMED 'CIPZ0003'**

(50) Latin Name: ***Campanula* interspecific**
Varietal Denomination: CIPZ0003

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,738

(22) Filed: Oct. 6, 2015

(65) Prior Publication Data

US 2017/0099765 P1 Apr. 6, 2017

(51) Int. Cl.
*A01H 5/02* (2006.01)

(52) U.S. Cl.
USPC ..... Plt./414

(58) Field of Classification Search
USPC ..... Plt./414
See application file for complete search history.

*Primary Examiner* — Keith O Robinson
(74) *Attorney, Agent, or Firm* — Dale Skalla

(57) ABSTRACT

A new *Campanula* plant named 'CIPZ0003' particularly distinguished by large, wide open, blue and white bicolored, star-shaped flowers, an early and floriferous flowering response, grass-green foliage with cordate leaves, medium vigorous growth, good-branching ability, compact, rounded mounding and even plant habit, is disclosed.

1 Drawing Sheet

Latin name of the genus and species of the plant claimed: *Campanula* interspecific.

Varietal denomination: 'CIPZ0003'.

BACKGROUND OF THE NEW PLANT

The present invention comprises a new and distinct cultivar of *Campanula*, botanically known as *Campanula* interspecific and hereinafter referred to by the cultivar name 'CIPZ0003'. The new cultivar originated from an open pollination made in February 2007 in Andijk, The Netherlands The female parent was 'C08-0005-1', a proprietary (unpatented) white-flowered *Campanula isophylla* plant, with bigger flowers, but less of them and a more vigorous habit, while the male parent was unknown.

The seeds produced by the hybridization were sown in August 2008 in Enkhuizen, The Netherlands and the resulting seedlings were selected in January 2009. A single plant selection was chosen for further evaluation and for asexual propagation in 2009.

The new cultivar was created in 2009 in Enkhuizen, The Netherlands and has been asexually reproduced repeatedly by vegetative cuttings and tissue culture in Enkhuizen, The Netherlands over a four year period. The present invention has been found to retain its distinctive characteristics through successive asexual propagations.

SUMMARY OF THE INVENTION

The following are the most outstanding and distinguishing characteristics of this new cultivar when grown under normal horticultural practices in Enkhuizen, The Netherlands 1. Large, wide-open, blue and white bicolor, star-shaped flowers;

2. An early and floriferous flowering response;
3. Grass-green foliage with cordate leaves;
4. Good branching ability;
5. Medium vigorous growth;
6. A compact, rounded, even and mounding plant habit.

BRIEF DESCRIPTION OF THE PHOTOGRAPHS

This new *Campanula* plant is illustrated by the accompanying photographs which show overall plant habit including blooms, buds, and foliage of the plant. The colors shown are as true as can be reasonably obtained by conventional photographic procedures. The photographs are of 4 month old plants grown in a greenhouse in Enkhuizen, The Netherlands in July 2013.

DESCRIPTION OF THE NEW CULTIVAR

Figure 1:
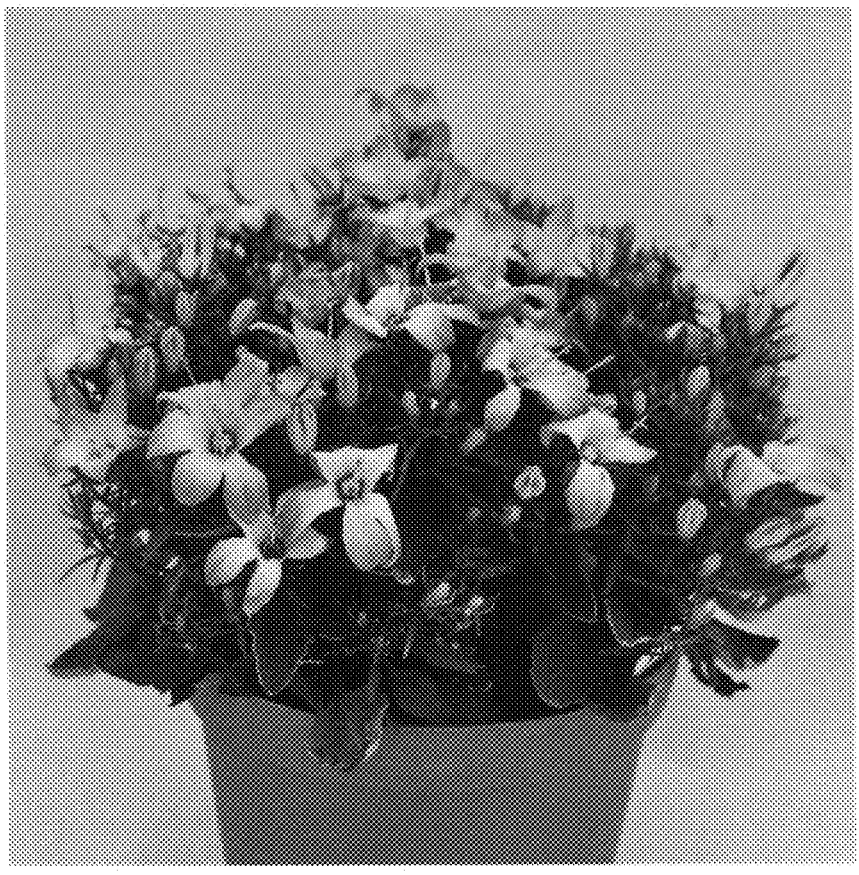
FIG. 1 shows the overall plant habit, including blooms, buds, foliage, and plant habit.
Figure 2:
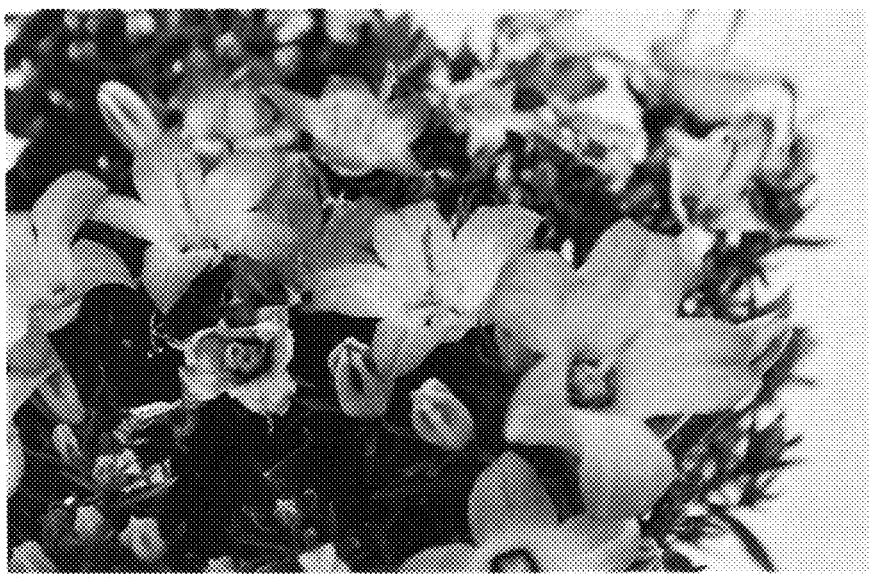
FIG. 2 shows a close-up of the mature inflorescences.

The following detailed description sets forth the distinctive characteristics of 'CIPZ0003'. The data which define these characteristics were collected from asexual reproductions carried out in Enkhuizen, The Netherlands. The plant history was taken on 13 week old plants that were once pinched. The plants were in 12 cm pots.

Color readings were taken under natural light. Color references are primarily to The R.H.S. Colour Chart of The Royal Horticultural Society of London (R.H.S.) (2001).

DETAILED BOTANICAL DESCRIPTION

Classification:

*Family.*—Campanulaceae.

*Botanical.*—*Campanula* interspecific.

*Parentage.*—Female parent 'C08-0005-1'. Male parent: Unknown.

TABLE 1

DIFFERENCES BETWEEN THE NEW VARIETY 'CIPZ0003' AND A MOST SIMILAR VARIETY

| | 'CIPZ0003' | 'Camp Bulewhit', U.S. Pat. No. PP18,726 |
|---|---|---|
| Earliness: | 2 weeks earlier | 2 weeks later |
| Leaf size: | Smaller | Bigger |
| Flower size: | Smaller | Bigger |
| Flower color: | Blue is more intense blue | Blue is more light blue |

Propagation:

*Type cutting.*—Terminal vegetative cuttings.

*Time to initiate roots.*—13 days at 18-21 degrees C.

*Root description.*—Fibrous, fine and cream-white RHS 1D.

*Growth.*—Form Herbaceous perennial.

Plant description:

*Form.*—Perennial, rosette plant with a mounding habit.

*Habit.*—Relatively compact, well branching, rounded plant habit.

*Crop time.*—After rooting, about 13 weeks to produce finished plants in a 12 cm pot.

*Plant height* (*soil level to top of plant plane*).—12-13 cm.

*Plant spread* (*width*).—18-24 cm.

*Vigor.*—Vigorous growth rate.

Foliage description:

*Arrangement.*—Alternate, simple.

*Size.*—Length: 2.4-2.6 cm. Width: 1.9-2.4 cm.

*Shape.*—Lower leaves: Ovate. Upper leaves: Lanceolate.

*Margin.*—Entire to slightly biserrate.

*Apex.*—Acute.

*Base.*—Obtuse.

*Color.*—Immature leaves: Upper surface: RHS 137B. Lower surface: RHS 138C. Mature leaves: Upper surface: RHS between 144B and 143A. Lower surface: RHS 147C.

*Texture.*—Very short hair on upper surface, very few, longer hair along the leaf veins of the lower surface.

*Venation.*—Palmate simple.

*Venation color.*—Upper surface: RHS 145A. Lower surface: RH 139D.

*Petioles.*—Length: Variable, up to 3.3 cm. Width: 0.13 cm. Color: Upper surface: RHS 145A with both sides/edges greener RHS 137B. Lower surface: RHS 139D with thin edges of RHS 138B. Texture: Pubescence on the upper part, fine short hair and longer ones, less dense along the sides.

*Variegation.*—Absent.

Stems:

*Average number of basal branches.*—25.

*Length.*—2-5 cm without inflorescence; up to 10 cm with inflorescence.

*Diameter.*—0.3 cm.

*Internode length.*—1.2-2.4 cm.

*Color.*—RHS 143B.

*Anthocyanin.*—None.

*Texture.*—Covered with very short pubescence.

*Average number of lateral branches.*—7.

*Branch diameter.*—0.1-0.2 cm.

*Leaves per lateral branch.*—5.

*Internode length.*—1.5 cm at base and 0.5 cm higher up.

*Color.*—RHS 143C.

Flower bud:

*Shape.*—Narrow and oval (elongated) with furrows.

*Size.*—Length: 1.4 cm. Diameter: 0.5 cm.

*Color closed bud.*—RHS 2D.

Inflorescence:

*Inflorescence type.*—Dischasium.

*Number of flowers per inflorescence.*—About 4 to 7 flowers and buds.

*Length.*—5 cm.

*Diameter.*—8 cm.

*Peduncles.*—Length: 2-4 cm. Diameter: 0.1 cm. Angle: 0 to 60 degrees from vertical. Color: RHS 138C. Texture: Fine pubescence.

*Pedicels.*—Length: 0.6 cm. Diameter: 0.1 cm. Color: RHS 143A. Anthocyanin: None. Texture: Fine pubescence.

Flowers:

*Flower type.*—Single, sympetalous, campanulate.

*Arrangement.*—Upward to spreading.

*Longevity.*—Individual flowers stay open for 3-5 days.

*Corolla.*—Shape: Wide open, shallow cup-shape; composed of 5 petals. Size: Diameter: 3.5 cm. Depth: 1.5-1.8 cm, including ovary. Color: Upper surface: Edge of 1.6 cm blue RHS 101B, center RHS whiter then 155C. Lower surface: RHS whiter then 155C.

*Petals.*—Shape: Roughly ovate. Arrangement: Fused at the base of the petal, on 1 cm, above this, the rest is free, curling backwards. Size: Length: 2 cm. Width: 1.2 cm. Apex: Broadly acute. Base: Fused. Margin: Entire. Texture: Glabrous.

*Calyx.*—Composed of 5 Sepals.

*Arrangement.*—Sepals fused at the base. Color (both surfaces): RHS 143B to RHS 144B. Length: 0.7 cm. Width: 0.15 cm. Shape: Narrow ovate. Apex: Acute. Base: Fused. Margin: Entire. Petaloid lobes: Absent. Texture of upper and lower surface: Glabrous.

*Natural flowering season.*—Continuous throughout the summer, continuous under long-day conditions. Season can be extended year round by long day treatments. Flowers persistent.

*Fragrance.*—None.

Reproductive organs:

*Stamens.*—Quantity: 5, fused at the base.

*Filament.*—Color: RHS 157D. Length: 0.4 cm, fused at the base. Diameter: 0.1 cm.

*Anther.*—Color: RHS N167C. Length: 0.35 cm. Diameter: 0.1 cm.

*Pollen.*—Color: RHS 164C. Amount: Moderate.

*Pistil.*—Quantity: 1. Length: 1.4 cm.

*Stigma.*—Color: RHS 151D. Length: 0.3 cm. Shape: 3-lobed, with hirsute pubescent surface on the upper surface.

*Style.*—Color: RHS 154D. Length: 0.7-1.2 cm.

*Ovary.*—Type: Syncarpous gynoecium. Shape: Oval. Length: 0.3 cm. Diameter: 0.4 cm. Color: RHS 155C.

*Fruit and seed set.*—None observed.

*Disease/pest resistance.*—Neither resistance nor susceptibility to the normal diseases and pests of *Campanula* has been observed.

*Drought tolerance and cold tolerance.*—Hardy perennial. Tolerates high temperature to at least 30 degrees C. Tolerates low temperatures to degrees minus 5 C. No specific drought tolerance has been observed.

What is claimed is:

1. A new and distinct variety of *Campanula* plant named 'CIPZ0003' substantially as illustrated and described herein.

* * * * *